US010639105B2

(12) United States Patent
Razeto et al.

(10) Patent No.: US 10,639,105 B2
(45) Date of Patent: May 5, 2020

(54) NAVIGATION APPARATUS AND METHOD

(71) Applicant: Toshiba Medical Systems Corporation, Otawara-shi (JP)

(72) Inventors: Marco Razeto, Edinburgh (GB); Takuya Sakaguchi, Utsunomiya (JP); Chris McGough, Edinburgh (GB)

(73) Assignee: Canon Medical Systems Corporation, Otawara-shi (JP)

( * ) Notice: Subject to any disclaimer, the term of this patent is extended or adjusted under 35 U.S.C. 154(b) by 213 days.

(21) Appl. No.: 15/825,893

(22) Filed: Nov. 29, 2017

(65) Prior Publication Data
US 2019/0159842 A1 May 30, 2019

(51) Int. Cl.
*G06K 9/00* (2006.01)
*A61B 34/20* (2016.01)
(Continued)

(52) U.S. Cl.
CPC .......... *A61B 34/20* (2016.02); *A61B 5/02007* (2013.01); *A61B 5/055* (2013.01); *A61B 6/032* (2013.01); *A61B 6/12* (2013.01); *A61B 6/4085* (2013.01); *A61B 6/463* (2013.01); *A61B 6/504* (2013.01); *A61B 8/0841* (2013.01); *A61B 17/3403* (2013.01); *A61B 34/10* (2016.02); *A61F 2/95* (2013.01); *A61M 25/09* (2013.01); *A61M 25/10* (2013.01); *G06T 7/74* (2017.01); *G06T 19/003* (2013.01); *G06T 19/20* (2013.01); *A61B 5/062* (2013.01); *A61B 6/481* (2013.01); *A61B 6/487* (2013.01); *A61B 6/5217* (2013.01); *A61B 2017/00778* (2013.01);
(Continued)

(58) Field of Classification Search
None
See application file for complete search history.

(56) References Cited

U.S. PATENT DOCUMENTS 9,697,603 B2   7/2017 Reynolds et al.
2008/0312673 A1  12/2008 Viswanathan et al.
(Continued)

OTHER PUBLICATIONS

"Philips Live Image Guidance in endovascular procedures", http://www.philips.co.uk/healthcare/clinical-solutions/live-image-guidance/treating-vascular-diseases/endovascular-oncology-therapy, Retrieved Aug. 21, 2017, 18 pages.
(Continued)

*Primary Examiner* — Atiba O Fitzpatrick
(74) *Attorney, Agent, or Firm* — Oblon, McClelland, Maier & Neustadt, L.L.P.

(57) ABSTRACT

A navigation apparatus for assisting navigation of a device through tissue comprises processing circuitry configured to receive volumetric medical imaging data representative of an anatomical region, the anatomical region comprising a region of tissue to be traversed by a device; process the volumetric medical imaging data to identify different types of tissue in the region of tissue; determine a position of the device; and process the volumetric medical imaging data to obtain a virtual endoscopic view of at least part of the region of tissue, the virtual endoscopic view comprising a virtual representation of the device in its determined position; wherein the virtual endoscopic view is rendered such as to visually distinguish the identified different types of tissue, thereby assisting navigation of the device through the region of tissue.

21 Claims, 4 Drawing Sheets

(51) Int. Cl.

| | | |
|---|---|---|
| G06T 7/73 | (2017.01) | |
| G06T 19/20 | (2011.01) | |
| A61B 17/34 | (2006.01) | |
| A61M 25/09 | (2006.01) | |
| A61B 5/055 | (2006.01) | |
| A61B 6/03 | (2006.01) | |
| A61B 6/00 | (2006.01) | |
| A61B 8/08 | (2006.01) | |
| A61F 2/95 | (2013.01) | |
| G06T 19/00 | (2011.01) | |
| A61B 34/10 | (2016.01) | |
| A61B 6/12 | (2006.01) | |
| A61B 5/02 | (2006.01) | |
| A61M 25/10 | (2013.01) | |
| A61B 90/00 | (2016.01) | |
| H04B 1/06 | (2006.01) | |
| A61M 25/01 | (2006.01) | |
| A61B 5/06 | (2006.01) | |
| A61B 17/00 | (2006.01) | |

(52) U.S. Cl.
CPC ... *A61B 2034/102* (2016.02); *A61B 2034/105* (2016.02); *A61B 2034/107* (2016.02); *A61B 2034/2051* (2016.02); *A61B 2034/2065* (2016.02); *A61B 2090/364* (2016.02); *A61B 2090/376* (2016.02); *A61B 2090/3762* (2016.02); *A61B 2090/3966* (2016.02); *A61M 2025/0166* (2013.01); *G06T 2207/10068* (2013.01); *G06T 2207/30101* (2013.01); *G06T 2210/41* (2013.01); *G06T 2210/62* (2013.01); *G06T 2219/2012* (2013.01); *H04B 1/06* (2013.01)

(56) References Cited

U.S. PATENT DOCUMENTS

| | | | |
|---|---|---|---|
| 2009/0016483 A1* | 1/2009 | Kawasaki | A61B 5/02007 378/4 |
| 2009/0087068 A1 | 4/2009 | Sakaguchi | |
| 2012/0063644 A1 | 3/2012 | Popovic | |
| 2016/0008083 A1* | 1/2016 | Kesten | A61B 5/062 600/424 |
| 2016/0335757 A1 | 11/2016 | Florent et al. | |

OTHER PUBLICATIONS

Marco Razeto, et al. "Accurate, Fully-Automated Registration of Coronary Arteries for Volumetric CT Digital Subtraction Angiography", Proc. of SPIE, vol. 9034, 90343F, 2014, 7 pages.

Sandor Miklos Szilagyi, et al. "Automatic Segmentation Techniques of the Coronary Artery Using CT Images in Acute Coronary Syndromes", Journal of Cardiovascular Emergencies, 3(1), 2017, 9 pages.

P. Markelj, et al. "A review of 3D/2D registration methods for image-guided interventions", Medical Image Analysis, vol. 16, Issue 3, 2012, 20 pages.

Lei XU, et al. "Virtual Intravascular Endoscopy Visualization of Calcified Coronary Plaques", Medicine, vol. 94, Issue 17, 2015, 11 pages.

* cited by examiner

NAVIGATION APPARATUS AND METHOD

FIELD

Embodiments described herein relate generally to a navigation apparatus and method, for example for assisting navigation of a device through tissue.

BACKGROUND

Chronic Total Occlusion (CTO) is a pathology where an artery (which may often be a coronary artery) is completely occluded by a build-up of plaque. It usually happens over time, and may often be treated via PI (percutaneous intervention), which may be a PCI (percutaneous coronary intervention).

During a percutaneous intervention, a guide wire may be pushed into a patient's arterial system all the way to a blockage. The blockage may comprise hard and/or soft plaque. The blockage may also be referred to as an occlusion.

Many techniques may require the guide wire to traverse the occlusion in some way. For example, the guide wire may traverse the blockage to allow the deployment of a catheter for the stenting or removal of the blockage.

FIG. 1a shows an example of an occlusion 16 in a vessel 10 having a vessel wall 12 and lumen 14. The vessel 10 is partially blocked by the occlusion 16. However, some patent lumen (unblocked lumen) is present at 18, allowing some blood to flow through the occlusion 16. Blood flow is represented by an arrow 19. The blood flow is constricted on entering the occlusion 16.

In FIG. 1b, a guide wire 20 carrying a dilation device 22 is threaded through the occlusion 16, and the dilation device 22 is used to dilate a stent 24 once the stent 24 is in position at the occlusion 16.

FIG. 1c shows the dilated stent 24 once the dilation device 22 has been removed. The stent 24 remains dilated and allows increased blood flow (represented by arrow 26) where previously the vessel was partially blocked by the occlusion 16.

Where a narrow passage through the occlusion in the artery is present (for example, as illustrated in FIG. 1), a surgeon may try to thread a small guide wire through the occlusion. The passage through the occlusion may often be small. The risk of perforating the artery or dislodging plaque and causing infarction may be considerable. In some circumstances, very little navigational information may be available.

In a case of complete occlusion, the surgeon may decide to attempt one of two techniques. In a first technique, the surgeon may push the guide wire through the blockage by navigating the wire through a soft component of the occlusion rather than hard component of the occlusion such as calcium. In a second technique, the surgeon may perform a subintimal crossing of the occlusion. In a subintimal crossing of the occlusion, the catheter creates a new channel between the intimal and medial layers of the vessel wall to bypass the plaque. The catheter should then re-enter the true lumen of the vessel. If the catheter does not re-enter the true lumen, a subintimal dissection may occur.

In some normal catheterization laboratory (cath-lab) interventions, fluoroscopy or X-ray angiography (XA) may be used to guide the progress of the guide wire. However, in the case of chronic total occlusion, visualization of an intervention may be difficult. Plaque may not be well imaged in fluoroscopy or X-ray angiography.

FIG. 2 shows an angiography image, in which vessels 30 appear near-black due to contrast enhancement of blood. The tip of a catheter is indicated by arrow 32. A guide wire 34 is shown pushing through a blockage. The material forming the blockage is not visible in X-ray angiography. Therefore, only limited navigational information may be provided by the X-ray angiography.

In some circumstances, very little information may be available regarding the composition of the material in front of the guide wire. For example, the material composition may not be apparent from an X-ray angiography image such as the image of FIG. 2.

BRIEF DESCRIPTION OF THE DRAWINGS

Embodiments are now described, by way of non-limiting example, and are illustrated in the following figures, in which.

DETAILED DESCRIPTION

Certain embodiments provide a navigation apparatus for assisting navigation of a device through tissue, the apparatus comprising processing circuitry configured to receive volumetric medical imaging data representative of an anatomical region, the anatomical region comprising a region of tissue to be traversed by a device; process the volumetric medical imaging data to identify different types of tissue in the region of tissue; determine a position of the device; and process the volumetric medical imaging data to obtain a virtual endoscopic view of at least part of the region of tissue, the virtual endoscopic view comprising a virtual representation of the device in its determined position; wherein the virtual endoscopic view is rendered such as to visually distinguish the identified different types of tissue, thereby assisting navigation of the device through the region of tissue.

Certain embodiments provide a navigation method for assisting navigation of a device through tissue, the method comprising receiving volumetric medical imaging data representative of an anatomical region, the anatomical region comprising a region of tissue to be traversed by a device; processing the volumetric medical imaging data to identify different types of tissue in the region of tissue; determining a position of the device; and processing the volumetric medical imaging data to obtain a virtual endoscopic view of at least part of the region of tissue, the virtual endoscopic view comprising a virtual representation of the device in its determined position; wherein the virtual endoscopic view is rendered such as to visually distinguish the identified different types of tissue, thereby assisting navigation of the device through the region of tissue.

Figure 1A:
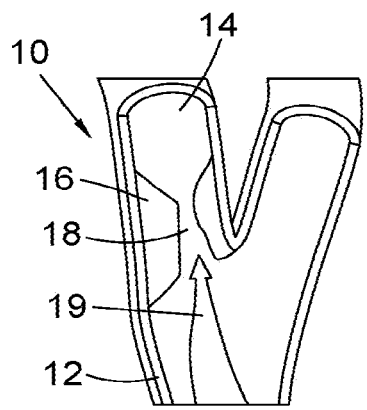
FIG. 1a is a schematic diagram illustrating a vessel having an occlusion.
Figure 1B:
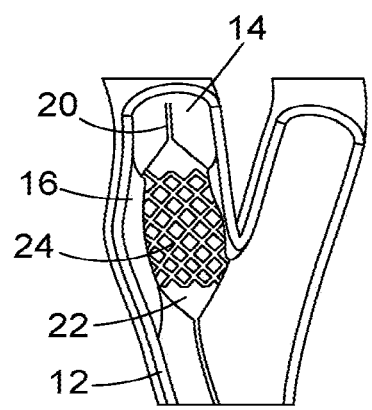
FIG. 1b is a schematic diagram illustrating dilation of the vessel by a dilation device.
Figure 1C:
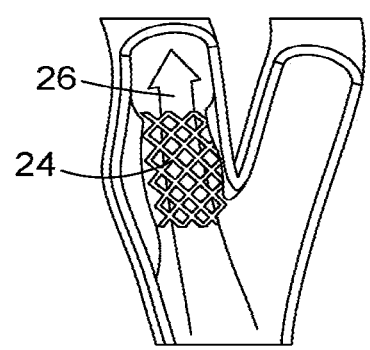
FIG. 1c is a schematic diagram illustrating a stent in the vessel.
Figure 2:
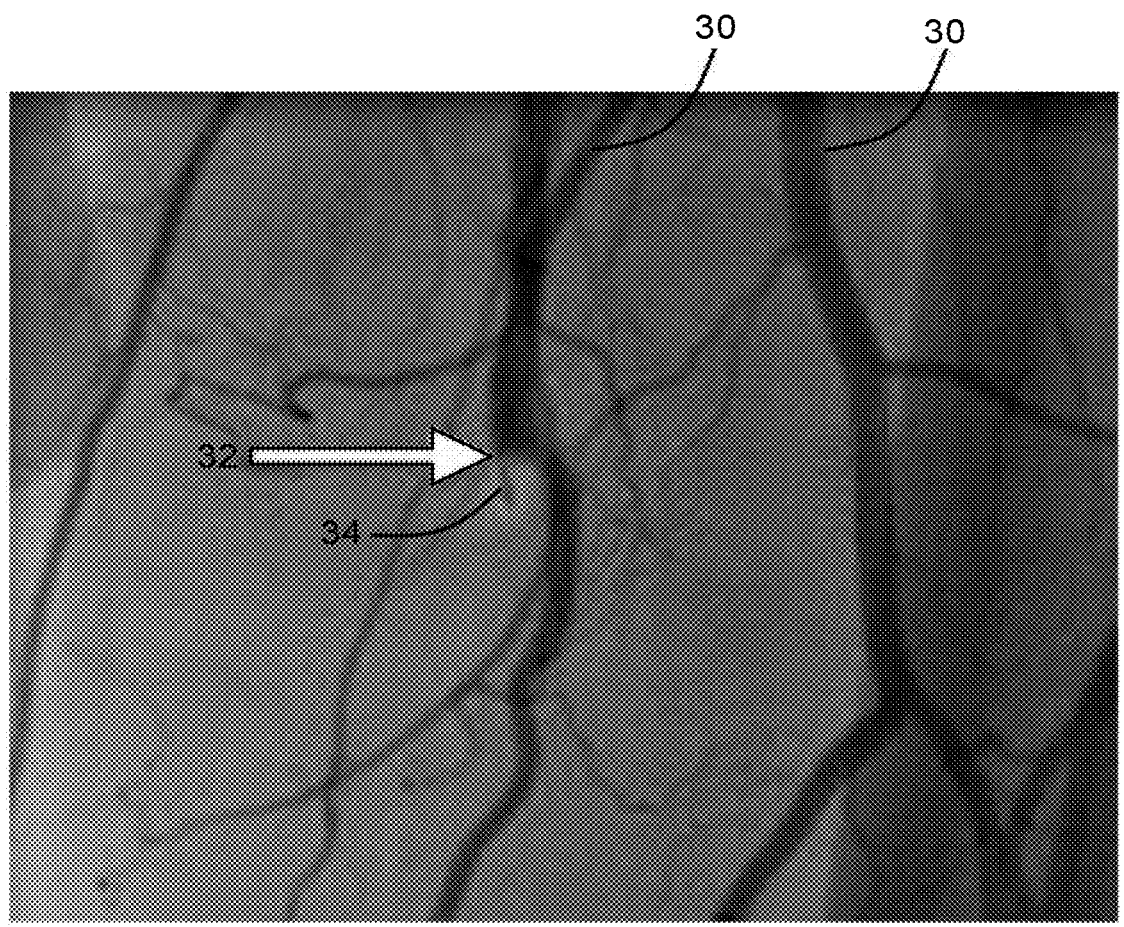
FIG. 2 is a angiography image showing a guide wire.
Figure 3:
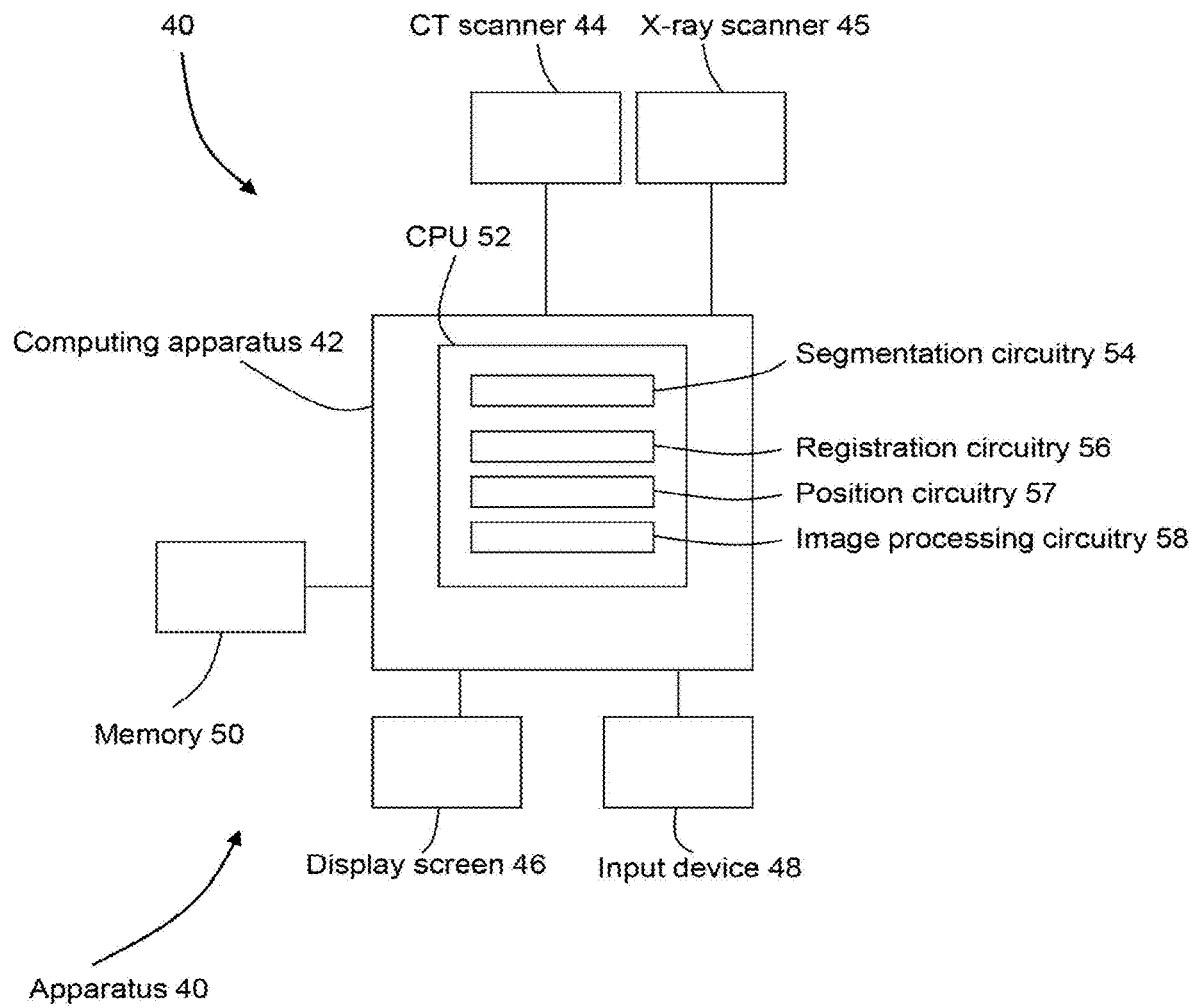
FIG. 3 is a schematic diagram of an apparatus in accordance with an embodiment.

An apparatus 40 according to an embodiment is illustrated schematically in FIG. 3. The apparatus 40 may be referred to as a navigation apparatus or virtual navigation apparatus.

The apparatus 40 comprises a computing apparatus 42, in this case a personal computer (PC) or workstation, which is connected to a computed tomography (CT) scanner 44, an X-ray scanner 45, one or more display screens 46 and an input device or devices 48, such as a computer keyboard, mouse or trackball.

The CT scanner 44 is configured to obtain volumetric CT data that is representative of an anatomical region of a patient or other subject. In the present embodiment, the volumetric CT data comprises non-contrast CT data and contrast-enhanced CT data.

In alternative embodiments, the CT scanner 44 may be replaced or supplemented by a scanner configured to obtain volumetric imaging data in any other imaging modality, for example a CT scanner, cone-beam CT scanner, MRI (magnetic resonance imaging) scanner or, ultrasound scanner. In some embodiments, volumetric imaging data may be obtained by acquiring multiple two-dimensional scans.

The X-ray scanner 45 is configured to obtain X-ray data that is representative of the same anatomical region of the same patient or other subject. In the present embodiment, the X-ray data comprises digital angiography data, digital subtraction angiography data and/or non-contrast X-ray data.

In the present embodiment, the X-ray data comprises two-dimensional data. In other embodiments, the X-ray scanner may be configured to obtain volumetric data.

In alternative embodiments, the X-ray scanner 45 may be replaced or supplemented by a scanner configured to obtain imaging data in any other imaging modality, for example a CT scanner, cone-beam CT scanner, MRI (magnetic resonance imaging) scanner, X-ray scanner, ultrasound scanner.

In the present embodiment, imaging data sets obtained by the CT scanner 44 and X-ray scanner 45 are stored in memory 50 and subsequently provided to computing apparatus 42. In an alternative embodiment, imaging data sets are supplied from a remote data store (not shown) which may form part of a Picture Archiving and Communication System (PACS). The memory 50 or remote data store may comprise any suitable form of memory storage.

In the present embodiment, the CT scanner 44 and X-ray scanner 45 are connected to the computing apparatus 42. In other embodiments the CT scanner 44 and/or X-ray scanner 45 may not be connected to the computing apparatus 42.

Computing apparatus 42 provides a processing resource for automatically or semi-automatically processing imaging data sets, and comprises a central processing unit (CPU) 52.

The computing apparatus 42 includes segmentation circuitry 54 configured to segment different tissue types in CT data; registration circuitry 56 configured to register CT data and X-ray data; position circuitry 57 configured to determine a position of a device; and image processing circuitry 58 configured to render a virtual endoscopy image in which the different tissue types may be distinguished, and in which a virtual representation of the device is displayed.

In the present embodiment, the circuitries 54, 56, 57, 58 are each implemented in computing apparatus 42 by means of a computer program having computer-readable instructions that are executable to perform the method of the embodiment. However, in other embodiments, the various circuitries may be implemented as one or more ASICs (application specific integrated circuits) or FPGAs (field programmable gate arrays).

The computing apparatus 42 also includes a hard drive and other components of a PC including RAM, ROM, a data bus, an operating system including various device drivers, and hardware devices including a graphics card. Such components are not shown in FIG. 3 for clarity.

Figure 4:
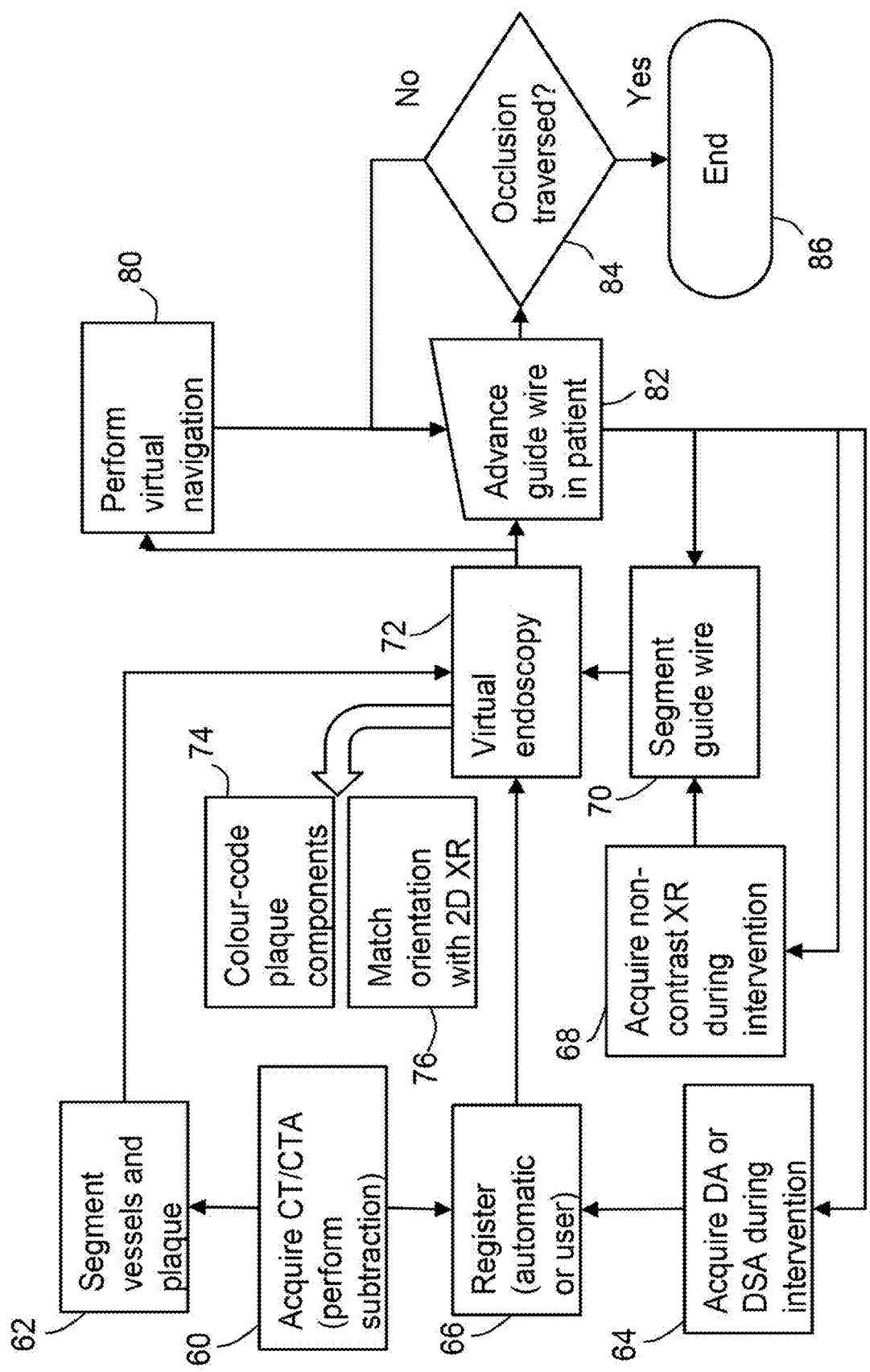
FIG. 4 is a flow chart illustrating in overview a method of an embodiment.

FIG. 4 is a flow chart illustrating in overview a method of an embodiment. In the embodiment of FIG. 4, the navigation apparatus 40 of FIG. 3 is used to assist a surgeon to navigate a guide wire 20 through an occlusion 16 in a vessel 10, by providing visual information about the types of plaque forming the occlusion 16.

At stage 60 of FIG. 4, the CT scanner 44 acquires volumetric CT data comprising a non-contrast CT data set (which may be referred to as a CT data set) and a contrast-enhanced CT data set (which may be referred to as a CTA data set). The non-contrast CT data set and contrast-enhanced CT data set are representative of an anatomical region of a patient. The non-contrast CT data set is obtained without a contrast agent being present in the anatomical region. The contrast-enhanced CT data set is obtained with a contrast agent present in the anatomical region.

In the present embodiment, the anatomical region comprises a vessel 10 that is at least partially blocked by an occlusion 16. In other embodiments, the anatomical region may be any region of interest of any human or animal subject. For example, the anatomical region may comprise any appropriate vessel and/or organ. The anatomical region may comprise any region of tissue that is to be traversed by a device as part of a surgical intervention, for example as part of any procedure in which the device is introduced into the body of a patient or other subject. In some embodiments, the anatomical region may comprise any type of occlusion or blockage.

The non-contrast CT data set and the contrast-enhanced CT data set are passed to the segmentation circuitry 54 and to the registration circuitry 56.

The registration circuitry 56 registers the non-contrast CT data set and the contrast-enhanced data set. Any suitable registration method may be used, for example Razeto, M., Mohr, B., Arakita, K., Schuijf, J. D., Fuchs, A., Kühl, J. T., Chen, M. Y., and Kofoed, K. F., "Accurate, fully-automated registration of coronary arteries for volumetric CT digital subtraction angiography," Proc. SPIE 9034, 90343F-90343F-7 (2014).

The registration circuitry 56 subtracts the registered non-contrast CT data set and contrast-enhanced CT data set to obtain a subtraction CT data set. Subtracting registered non-contrast data and contrast-enhanced data may remove features that are common to the contrast-enhanced data and non-contrast data, for example bone or soft tissue, to leave parts of the contrast-enhanced data that have been enhanced by the contrast agent.

At stage 62, the segmentation circuitry 54 performs a segmentation of the contrast-enhanced CT data set.

In general, segmentation may be the process of identifying pixels or voxels representing a given structure in an image, which may include separating the pixels or voxels from the rest of the image. The structure may be, for example, an anatomical structure such as a bone, a vessel or an organ. The structure may be a region of a particular tissue type, for example soft plaque, hard plaque, vessel wall or lumen. The pixels or voxels may be classified as belonging to a particular tissue type. A probability of each pixel or voxel belonging to each tissue type may be calculated.

In the present embodiment, the segmentation performed by the segmentation circuitry 54 comprises an image-based segmentation. In other embodiments, any suitable segmentation method may be used. For example, the segmentation method may be a method as referenced in Szilágyi, S., Popovici, M. & Szilágyi, L. (2017). Review. Automatic Segmentation Techniques of the Coronary Artery Using CT Images in Acute Coronary Syndromes. *Journal Of Cardio-*

*vascular Emergencies,* 3(1), pp. 9-17, which described various different techniques to segment plaque in blood vessels, in particular coronary blood vessels.

In some embodiments, the segmentation method may comprise using information from both the contrast-enhanced CT data set and the non-contrast CT data set, for example as described in U.S. Pat. No. 9,697,603.

The segmentation comprises identifying voxels that are representative of different tissue types. Voxels may be labelled as belonging to a particular tissue type. Voxels may be assigned a probability of belonging to each tissue type.

The segmentation method of the present embodiment characterizes the plaque in the contrast-enhanced CT data set by distinguishing hard (calcified) plaque from soft plaque. The tissue types identified in the segmentation of the present embodiment comprise hard plaque, soft plaque, vessel wall, and vessel lumen.

In other embodiments, any tissue types may be segmented. The different tissue types may comprise tissue of any different anatomical structures, for example different organs.

In the present embodiment, stages 60 and 62 are performed before the start of a surgical intervention. For example, the CT scanner may acquire the CT data of stage 60 some hours before the surgical intervention. The timing of stage 60 may be close enough to the time of the intervention that the CT data acquired at stage 60 may be considered to be representative of the state of the anatomical region during the surgical intervention, for example the extent of the occlusion.

At stage 64, the surgical intervention begins. In the present embodiment, the surgical intervention is a percutaneous intervention. In other embodiments, the surgical intervention may be any appropriate type of surgical intervention. In some embodiments, the surgical intervention may comprise endoscopy or arthroscopy.

A contrast agent is introduced into the vasculature of the patient, such that contrast material is present in the anatomical region of interest. The X-ray scanner 45 acquires X-ray data which in the present embodiment comprises an initial digital subtraction angiography (DSA) data set. In other embodiments, the X-ray data acquired at stage 64 may comprise a digital angiography (DA) data set. The initial DSA data set is representative of the vasculature being treated.

In other embodiments, any suitable method may be used to acquire image data representative of the anatomical region at stage 64, for example cone-beam CT. The data acquired may be two-dimensional or three-dimensional.

At stage 66, the registration unit 54 registers the subtraction CT data set and the initial DSA data set. Any suitable registration method may be used to register the subtraction CT data set and the initial DSA data set. For example, the subtraction CT data set and the initial DSA data set may be registered using a method as described in P. Markelj, D. Tomaževič, B. Likar, F. Pernuš, A review of 3D/2D registration methods for image-guided interventions, In Medical Image Analysis, Volume 16, Issue 3, 2012, Pages 642-661 In the present embodiment, rigid registration is used. In other embodiments, the registration may comprise a locally deformable registration.

In further embodiments, the contrast-enhanced CT data set may be registered with the initial DSA data set instead of or in addition to the registration of the subtraction CT data set and the initial DSA data set.

In the present embodiment, the registration method of stage 66 is automated. However, in other embodiments, the registration may be semi-automatic or manual. For example, the registration circuitry may render images from the subtraction CT data set and the initial DSA data set and display the images on display screen 16 or on a further display. A user (for example, a radiographer) may manually align the images to obtain a registration between the subtraction CT data set and the initial DSA data set.

The registering of the subtraction CT data set and the initial DSA data set relates a coordinate system of the subtraction CT data set to a coordinate system of the initial DSA data set. The registering of the subtraction CT data set and the initial DSA data set may be considered to provide an initial alignment between CT images and X-ray images. In some circumstances, it may be expected that a coordinate system of subsequent X-ray data acquired by the X-ray scanner 45 during the intervention may be similar to the coordinate system of the initial DSA data set.

In the present embodiment, the image processing circuitry 58 performs image fusion of the initial DSA data set and the contrast-enhanced CT data set to obtain a fusion image. In other embodiments, the image processing circuitry 57 may generate a fusion image using CT data from any of the contrast-enhanced CT data set, the non-contrast CT data or the subtraction CT data set.

The fusion image may be displayed on display screen 46 or on a further display.

The fusion image is presented in the coordinate space of the initial DSA data set, such that no warping of the initial DSA data set takes place. By presenting the fusion image in the space of the initial DSA data set, the fusion image may be representative of the current state of the vasculature. The fusion image may present to a user (for example, a surgeon) an enhanced version of an expected DSA view.

In further embodiments, any appropriate view of the data acquired at stage 64 may be obtained, and may be displayed on the display screen 46 or further display. For example, initial DSA data may be processed to obtain a two-dimensional DSA view which may not comprise a fusion image. Initial DA data may be processing to obtain a two-dimensional DA view.

At stage 68, the surgeon inserts the guide wire 20 into the vasculature of the patient. The guide wire 20 is guided by the surgeon towards the anatomical region of interest, which in the present embodiment comprises the occlusion 16. X-ray scanner 45 is used to acquire further X-ray data. The further X-ray data may be acquired continuously, or at regular intervals, while the guide wire 20 is being inserted into the patient.

In the present embodiment, the further X-ray data comprises non-contrast X-ray data. The further X-ray data may also comprise DA (Digital Angiography) and/or DSA (Digital Subtraction Angiography) data. The further X-ray data may comprise fluoroscopy data. Fluoroscopy is the name that may typically be used for continuously acquired X-ray in a interventional setting.

In other embodiments, the further X-ray data may be replaced or supplemented by data of any suitable modality, for example cone-beam CT data.

At stage 70, the position circuitry 57 segments pixels representing the guide wire 20 in the non-contrast X-ray data acquired at stage 68. The non-contrast X-ray data may be referred to as tracking data, since it is used to track the position of the guide wire 20. In the present embodiment, the guide wire is segmented using intensity thresholding of the non-contrast X-ray data. In other embodiments, any suitable method for segmenting the guide wire 20 may be used. For example, the guide wire 20 may be segmented based on its intensity in the non-contrast X-ray image. The segmentation of the guide wire 20 may use a template that is representative of the size and shape of the guide wire 20.

The position circuitry 57 determines a position of the guide wire 20 based on the segmentation of the further X-ray data. The determined position of the guide wire 20 comprises a position for a portion of the guide wire 20 comprising the tip of the guide wire 20. The portion of the guide wire 20 for which a position is determined is within or near the anatomical region of interest. The position may comprise a plurality of respective positions for points on the portion of the guide wire, including a position for the tip of the guide wire 20.

In other embodiments, any suitable tracking data and method of processing the tracking data may be used to determine a position of the guide wire 20. The tracking data may or may not comprise non-contrast X-ray data. The method of processing the tracking data may or may not comprise segmenting pixels representative of the guide wire 20 in the tracking data. For example, in some embodiments electromagnetic tracking of the guide wire is used to determine the position of the guide wire 20. In further embodiments, direct segmentation of the guide wire 20 may be performed using a thresholding and path tracking method to get to the tip of the guide wire 20. In some embodiments, a radiopaque marker is positioned at the tip of the guide wire 20 to assist position determination.

The position that is determined by the position circuitry for the guide wire 20 is in the coordinate space of the further X-ray data.

Stages 60 to 70 may be considered to provide a registration and localization stage. In stages 60 to 70, registration between the subtraction CT data set and initial DSA data set is followed by localization of the guide wire.

At stage 72, the image processing circuitry 58 generates a virtual representation 110 of the guide wire 20 using the determined position of the guide wire 20. The image processing circuitry 58 may make use of known information about the guide wire 20, for example a diameter of the guide wire 20 and a shape of the guide wire tip.

The image processing circuitry 58 processes the contrast-enhanced CT data set to obtain a virtual endoscopic view comprising the virtual representation 110 of the guide wire 20. The virtual endoscopic view is a simulated three-dimensional image showing at least part of the region of tissue through which the guide wire is to pass (which in this embodiment comprises the occlusion 16).

The virtual endoscopic view is rendered as if viewed from the position of a virtual camera. The virtual camera is positioned such that the virtual endoscopic view shows an end portion of the virtual representation 110 of the guide wire 20 that includes a representation of the guide wire tip. In the present embodiment, the virtual endoscopic view represents the vessel 18 as if it were viewed by an endoscope travelling down the vessel, although no such endoscope is actually present. The virtual endoscopic view provides an intraluminal view of the vessel. The virtual endoscopic view may make use of perspective projection such that proximal parts of the anatomical structure appear larger than distal parts.

In the present embodiment, the virtual endoscopic view is rendered from a virtual camera position that is inside the vessel. In other embodiments, the virtual endoscopic view may be rendered from any virtual camera position, which may be inside or outside a body part of interest, for example inside or outside a vessel lumen.

Any appropriate lighting method may be used in the rendering, for example global illumination.

In the present embodiment, the virtual endoscopic view is rendered from the contrast-enhanced CT data set, which is transformed into the coordinate space of the further X-ray data. The further X-ray data is being acquired during the surgical intervention. The further X-ray data may be considered to be acquired in real time. The further X-ray data may be considered to be representative of the current state of the patient. The transforming of the contrast-enhanced CT data set into the coordinate space of the further X-ray data may be based on the registration of the subtraction CT data set with the initial DSA data set at stage 66 and/or further registrations, for example registration of the further X-ray data set with the initial DSA data set. The further X-ray data may be registered to the subtraction CT data set, for example using a method as described in P. Markelj, D. Tomaževič, B. Likar, F. Pernuš, A review of 3D/2D registration methods for image-guided interventions, In Medical Image Analysis, Volume 16, Issue 3, 2012, Pages 642-661. The subtraction CT data set may provide information about plaque and vessel shape.

The image processing circuitry 58 applies the tissue segmentation obtained from the segmentation of the subtraction CT data set at stage 62 to the contrast-enhanced CT data set. The image processing circuitry 58 renders the virtual endoscopic view such that the different tissue types that were segmented at stage 62 are visually distinguished in the virtual endoscopic view. The different tissue types are visually distinguished by being rendered using different values for at least one rendering parameter, for example a color, a greyscale, an intensity, an opacity, a transparency, a lighting parameter, a texture parameter, a surface parameter, a reflection parameter, a type of rendering procedure. Visually distinguishing the different tissue types may comprise applying any artificial visual distinction between the tissue types in the rendered image, for example artificially coloring the different tissue types in different colors.

Figure 5:
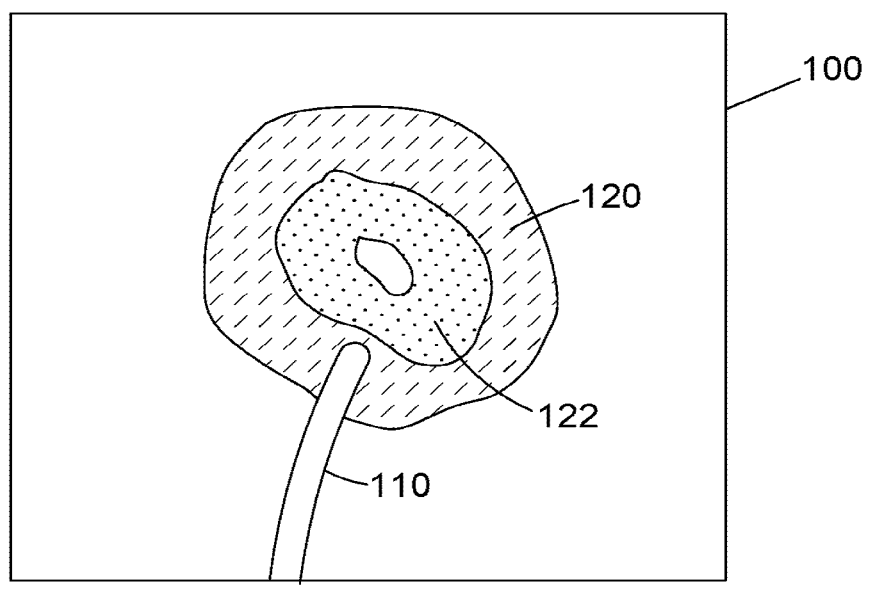
FIG. 5 is a schematic representation of a virtual endoscopic view.

FIG. 5 is a schematic diagram of a virtual endoscopic view of an occlusion comprising calcified plaque 120 and soft plaque 122. The image shown in FIG. 5 represents the guide wire 20 when it is approaching, but has not yet reached, the occlusion.

In the schematic diagram, the calcified plaque 120 and soft plaque 122 are visually distinguished in the virtual endoscopic view by being differently shaded. In the embodiment of FIG. 4, the calcified plaque 120 and soft plaque 122 are visually distinguished by being rendered in different colors. In other embodiments, any suitable method of visually distinguishing different tissue types may be used. For example, different color, greyscale or opacity values or other different rendering parameter values may be used to distinguish different types of tissue.

Although only the calcified plaque 120 and soft plaque 122 are shaded in FIG. 5, in practice the vessel wall is also distinguished in the virtual endoscopic view. In other embodiments, any types of tissue may be visually distinguished in any suitable manner.

In the method of FIG. 4, the virtual endoscopic view shows the calcified plaque 120 and soft plaque 122 as being partially transparent, for example semi-transparent. (This partial transparency is not shown in the schematic illustration of FIG. 5.) Since the calcified plaque 120 and soft plaque are partially transparent, the surgeon (or other viewer) is able to see through the surface of the occlusion in the virtual endoscopic view. By allowing some visibility through the surface of the occlusion, the surgeon may obtain information about the composition of the occlusion.

By seeing beyond the surface of the plaque, the surgeon may visualize the composition of the blockage and plan a path for the guide wire. Even visibility of a few millimeters beyond the surface may provide valuable information.

By rendering tissue as partially transparent, the virtual endoscopic view may provide a view that a real intraluminal endoscope may not be able to provide (because the real intraluminal endoscope may only be able to see as far as a tissue surface).

In the embodiment of FIG. 4, a degree of transparency of the tissue as displayed in the virtual endoscopic view is dependent on a distance from the tip of the virtual guide wire 110. Tissue near the tip of the virtual guide wire 110 is rendered as being more transparent than tissue further from the tip of the virtual guide wire 110. For example, there may be a linear decrease in transparency with distance from the position of the tip of the virtual guide wire 110. In other embodiments, all of the tissue represented in the virtual endoscopic view is represented with a constant value for transparency. In further embodiments, the transparency may vary with distance from the viewer, for example such that tissue that appears to be further from a viewer of the virtual endoscopic view also appears to be more opaque.

Elements 74 and 76 of the flow chart of FIG. 4 describe features of the virtual endoscopic view of stage 72. Element 74 indicates that plaque components are color-coded, as described above. For example, soft plaque 122 may be rendered in one color and hard plaque 120 in another, different color. By color-coding the vessel wall and the different plaque components, the shape of the vessel and the plaque ahead may be made very clear to the surgeon.

Element 76 indicates that the orientation of the virtual endoscopic view is matched with that of a 2D X-ray image.

In the present embodiment, the virtual endoscopic view 100 is displayed on the display screen 16 alongside a 2D X-ray image that is obtained by processing the non-contrast X-ray data that is being obtained in real time. The 2D X-ray image may be referred to as an angiogram. In other embodiments, a fusion image may be displayed instead of or in addition to the angiogram.

The virtual endoscopic view 100 is matched with the 2D X-ray image such that, for example, the left side of the virtual endoscopic view 100 corresponds to the left side of the 2D X-ray image, and the right side of the virtual endoscopic view 100 corresponds to the right side of the 2D X-ray image.

An orientation of the virtual endoscopic view 100 is set so that it matches an orientation of the guide wire 20 in the angiogram. The virtual endoscopic view 100 is oriented such that, for example, a clockwise rotation of the guide wire 20 in real life is shown as a clockwise rotation of the virtual guide wire 110 in the virtual endoscopic view 100. The orientation may allow easier control of the guide wire 20, as movement in a certain direction in the 2D angiography matches the movement in the virtual endoscopy.

At stage 80, the surgeon uses the virtual endoscopic view 100 to perform a virtual navigation process, which may be described as virtual guide wire navigation or virtual needle navigation.

In the virtual navigation process, the progress of the guide wire 20 in the current direction is simulated by the virtual guide wire 110. An animated sequence of images is generated in which the virtual guide wire 110 appears to move relative to the vessel. The virtual camera position from which the images are rendered may also be updated in order to follow the movement of the virtual guide wire 110. The virtual guide wire 110 is moved in the simulated three-dimensional image without any movement of the real guide wire 20 being performed.

For example, starting from the virtual endoscopic view 100 of FIG. 5, the virtual guide wire 110 moves forward, virtually advancing through the blockage. The virtual guide wire 110 may be moved in response to input from the surgeon or another user. The physician may use the virtual movement of the virtual guide wire 110 to plan a path through the blockage.

As the virtual guide wire 110 moves into the blockage, tissue from the surface of the blockage may be removed from the virtual endoscopic view so that the surgeon can see further into the blockage.

By using the virtual navigation process of stage 80, the surgeon determines whether the path that has been simulated in the virtual navigation process is likely to be successful. In some circumstances, the surgeon determines that the path that has been simulated is unlikely to be successful, for example because tissue that is further into the blockage is not as originally expected. The surgeon may repeat the virtual navigation process of stage 80, for example with a different movement of the virtual guide wire 110.

The virtual navigation process of stage 80 provides information to the surgeon that allows the surgeon to plan the next movement of the real guide wire 20.

At stage 82 of FIG. 4, the surgeon advances the guide wire 20 in the patient. The movement of the guide wire 20 may be small. The guide wire 20 may be moved by less than 5 mm, for example 1 mm.

Non-contrast X-ray data is still being obtained as the guide wire 20 is advanced in the patient. From the non-contrast X-ray data, the position circuitry 57 determines an updated position of the guide wire 20, including an updated position of the tip of the guide wire 20. The position circuitry 57 updates the position of the virtual guide wire 110 in the virtual endoscopic view 100 based on the updated position of the real guide wire 20.

It should be noted that the position of the virtual guide wire 110 obtained at stage 82 in response to the movement of the guide wire 20 may be different to the position of the virtual guide wire 110 at the end of the simulated movement of stage 80. For example, the guide wire 20 may not move exactly as planned and/or the vessel may be deformed as the guide wire moves through the vessel. The virtual endoscopic view may be updated to take into account changes in anatomy, for example deformation of the vessel. For example, the 2D non-contrast X-ray data and 3D CT data may be re-registered. The vessels may be realigned after each movement of the guide wire 20.

In other embodiments, the virtual endoscopic view may be updated based on any estimated or determined location of the tip of the guide wire 20, which may be obtained in any suitable manner.

At stage 84 of FIG. 4, the position circuitry 57 determines whether the occlusion has been traversed based on the position of the guide wire 20 and the segmentation obtained at stage 62. In other embodiments, the surgeon or other user may determine whether the occlusion has been traversed, or any suitable method may be used to determine whether the occlusion has been traversed.

If the occlusion has been traversed, the process of FIG. 4 proceeds to stage 86, at which the process ends.

If the occlusion has not yet been traversed, the process of FIG. 4 returns to stage 80. The surgeon performs a further virtual navigation process, which now starts from the updated position of the guide wire 20. The updated position of the guide wire 20 is shown in the virtual navigation view 100 as an updated position of the virtual guide wire 110.

The surgeon moves the virtual guide wire 110 forward from the updated position. The virtual endoscopic view shows the movement of the virtual guide wire 110. Optionally, the surgeon may repeat the virtual movement of the virtual guide wire 110 with different parameters, for example by moving the virtual guide wire 110 in a different direction.

When the surgeon is satisfied with the movement of the virtual guide wire 110, the method of FIG. 4 proceeds to stage 82 and the surgeon further advances the guide wire 20 in the patient.

The virtual endoscopic view 100 is updated to show a further position of the virtual guide wire 110 corresponding to the further position of the guide wire 20.

Stages 80 to 84 are repeated until the occlusion is traversed and the method of FIG. 4 ends at stage 86. Stages 80 to 84 may be considered to provide a virtual endoscopy stage.

By using a navigation method as described above, a surgeon (or other user) may obtain increased information about tissue through which the guide wire is to pass, which in this embodiment is an occlusion. By showing different tissue types such that they are visually distinguished (for example, in different colors), the virtual endoscopic view may provide additional information to the user beyond that present in the X-ray data (for example, DA, DSA or non-contrast X-ray data).

By using an iterative process of small movements, each planned using the navigation method, improved navigation of the occlusion may be achieved. Using small movements may mean that any differences between the simulated image and the real anatomy may have only a limited impact on the navigation process. Updating the image in response to real-time X-ray data may in some circumstances allow inaccuracies in the simulated view to be corrected. Updating the image in response to real-time data may allow deformation of the vessel during the procedure to be taken into account.

In some circumstances, the surgeon may use the additional information to plan a path more accurately than may otherwise be possible. Moving a virtual guide wire before moving a real guide wire may allow information from further into the blockage to be obtained before moving the real guide wire into the blockage. Moving a virtual guide wire before moving a real guide wire may allow different approaches to be simulated before performing a real movement.

In the embodiment of FIG. 4, the virtual guide wire is placed in a position that is representative of its real position in the vessel. The position of the guide wire (and therefore the viewing point of the simulated image) need not be in a predetermined position relative to the vessel, for example on a center line of the vessel.

Showing the different tissue types near the tip of the guide wire as partially transparent may allow the surgeon to see what is beyond the surface of the blockage (or other tissue), which may assist in path planning. The surgeon may see a representation of the tissue that is present if they move the guide wire forward into the blockage.

The method of FIG. 4 may provide a guidance solution based on registration between CT and DA or DSA, presentation of results in a virtual endoscopic view, visualization of plaque composition using color-coded segmentation, virtual navigation, and a progressive update of the visualization as the procedure progresses.

In the embodiment described above with reference to FIG. 4, a guide wire is guided through a blockage using virtual navigation. In other embodiments, any suitable device may be guided through any suitable tissue. The navigation process of FIG. 4 may be used for any surgical procedure in which navigation may otherwise be difficult.

For example, the device may comprise a catheter or a needle. A position of the catheter or needle may be obtained using any suitable position determination method. A virtual catheter or needle may be pictured in the virtual endoscopic view.

The region of tissue through which the device is navigated may comprise any appropriate vessel. In other embodiments, the region of tissue may comprise any appropriate tissue, for example any appropriate organ.

For example, transjugular intrahepatic portosystemic shunt (TIPSS) is an intervention in which a device may enter a first vessel then traverse a part of the liver to reach a second vessel. The virtual navigation process described above with reference to FIG. 4 may be used to navigate through the liver tissue from the first vessel to the second vessel. In further embodiments, the virtual navigation process may be used in other shunting interventions with different organs and/or vessels. The virtual navigation process may be applied to any percutaneous intervention, for example coronary stenting, tumor ablation and embolization, or neuro vascular interventions.

Certain types of medical imaging are described above as being performed at certain times during an intervention. However, in other embodiments any suitable types and timings of scans may be used. For example, although only an initial DSA data set is described above, in some embodiments one or more further DSA scans may be obtained during the intervention. A contrast agent may be introduced at various times during the intervention, for example before or after an important stage of the intervention takes place.

In the embodiment of FIG. 4, non-contrast CT data and contrast-enhanced CT are obtained and are used to generate subtraction CT data. In other embodiments, only contrast-enhanced CT data is obtained before the intervention and the contrast-enhanced CT data is registered to X-ray data obtained before or during the intervention. In further embodiments, references above to one of non-contrast X-ray data, contrast X-ray data, subtraction X-ray data, digital angiography data or digital subtraction angiography data may be replaced with references to another of non-contrast X-ray data, contrast X-ray data, subtraction X-ray data, digital angiography data or digital subtraction angiography data. References to one of non-contrast CT data, contrast CT data or subtraction CT data may be replaced with reference to another of non-contrast CT data, contrast CT data or subtraction CT data.

Although embodiments above are described as being performed by a surgeon, the embodiments or various stages of the embodiments may be performed by any appropriate user, for example any clinician, surgeon, physician, radiologist or radiographer.

In further embodiments, a navigation method as described above may be used for planning without a device having yet been introduced into the patient. For example, a virtual endoscopic view may be rendered from CT data without any X-ray data having yet been obtained. A user may view a virtual endoscopic view showing an occlusion (or other tissue). The user may navigate within the virtual endoscopic view to view the different tissue types within the blockage. The user may therefore obtain information about the blockage before the surgical intervention takes place. In some embodiments, a virtual guide wire may be positioned in the virtual endoscopic view without a real guide wire having been positioned inside the patient or other subject.

Certain embodiments provide a method of crossing an occlusive vascular lesion with a remotely actuated interventional device, comprising:

a) Acquiring CT/CTA and DA/DSA studies of the patient;
b) Segmenting plaque components from CT/CTA volumes;
c) Registering CT/CTA and DA/DSA;
d) Identifying location of guide wire tip in DA/DSA volumes;
e) Presenting virtual endoscopic view centered at location of the guide wire tip, in which segmented plaque components are color-coded according to step b);
f) Applying a virtual movement to the position of the guide wire identified in step d), thus simulating the advancement of the guide wire tip in the virtual endoscopy;
g) Updating the virtual endoscopic view when the virtual position of the guide wire has changed, thus displaying the composition of the plaque beyond the real location of the guide wire;
h) Iterating step e to g until the desired path of the guide wire is decided;
i) Advancing the guide wire according the path decided in step h);
j) Iterating steps d to i until the guide wire has traversed the occlusive vascular lesion.

Step c) may be performed via an automatic, semi-automatic, or manual method. Step e) may also comprise the alignment of the frames of reference of the virtual endoscopy with the frames of reference of the DA/DSA volumes. The segmentation of the plaque components in step e) may be presented in a semi-transparent rendering in which the transparency transfer function is controlled by distance from the wire tip.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A navigation apparatus for assisting navigation of a device through tissue, the apparatus comprising processing circuitry configured to:
receive volumetric medical imaging data representative of an anatomical region, the anatomical region comprising a region of tissue to be traversed by a device;
process the volumetric medical imaging data to identify different types of tissue in the region of tissue, wherein the different types of tissue comprise soft plaque and hard plaque;
determine a position of the device; and
process the volumetric medical imaging data to obtain a virtual endoscopic view of at least part of the region of tissue, the virtual endoscopic view comprising a virtual representation of the device in its determined position;
wherein the virtual endoscopic view is rendered such as to visually distinguish the identified different types of tissue, thereby assisting navigation of the device through the region of tissue.

2. An apparatus according to claim 1, wherein the virtual endoscopic view is rendered such that at least some of the region of tissue is at least partially transparent in the virtual endoscopic view, thereby providing visibility beyond a surface of the region of tissue.

3. An apparatus according to claim 1, wherein the device comprises a device configured to be used as part of a surgical intervention.

4. An apparatus according to claim 1, wherein the determined position of the device comprises a current position of the device, wherein the device is positioned in the anatomical region.

5. An apparatus according to claim 1, wherein the processing circuitry is further configured to simulate a movement of the device into or through the region of tissue.

6. An apparatus according to claim 1, wherein the anatomical region comprises a vessel, the region of tissue comprises an occlusion in the vessel, and the navigation of the device through the region of tissue comprises navigation of the device through or around the occlusion.

7. An apparatus according to claim 1, wherein the different types of tissue further comprise a vessel wall.

8. An apparatus according to claim 1, wherein the device comprises at least one of a guide wire, a catheter, a needle.

9. An apparatus according to claim 1, wherein the processing circuitry is further configured to:
determine a further position of the device; and
update the virtual endoscopic view in accordance with the further position of the device.

10. An apparatus according to claim 1, wherein the determining of the current position of the device is based on real-time tracking data, the real-time tracking data comprising at least one of X-ray data, fluoroscopy data, digital angiography data, digital subtraction angiography data, electromagnetic data.

11. An apparatus according to claim 1, wherein the processing circuitry is further configured to obtain second medical imaging data representative of the anatomical region, the second medical imaging data comprising at least one of X-ray data, fluoroscopy data, digital angiography data, digital subtraction angiography data and to process the second medical imaging data to obtain a two-dimensional view of the anatomical region.

12. An apparatus according to claim 11, wherein the processing circuitry is further configured to set an orientation of the virtual endoscopic view to match an orientation of the device as represented in the two-dimensional view, and wherein the virtual endoscopic view is oriented such that a movement of the device is represented by a corresponding movement of the virtual representation of the device in the virtual endoscopic view.

13. An apparatus according to claim 1, wherein the rendering of the virtual endoscopic view comprises rendering each of the different tissue types using different values for at least one rendering parameter, the at least one rendering parameter comprising at least one of a color, a greyscale, an intensity, an opacity, a transparency, a lighting parameter, a texture parameter, a surface parameter, a reflection parameter, a type of rendering procedure.

14. An apparatus according to claim 1, wherein the different tissue types are distinguished in the virtual endoscopic view by at least one of different color, different transparency.

15. An apparatus according to claim 1, wherein a level of transparency of tissue in the virtual endoscopic view is dependent on a distance from the current position or a simulated position of the device and/or a level of transparency of tissue in the virtual endoscopic view is dependent on a distance from a viewing position.

16. An apparatus according to claim 1, wherein the volumetric medical imaging data comprises at least one of CT data, contrast-enhanced CT data, CT subtraction data, MR data, ultrasound data.

17. An apparatus according to claim 1, wherein the processing circuitry is further configured to register the volumetric medical imaging data with further medical imaging data representative of the anatomical region, and a position of the virtual representation of the device in the virtual endoscopic view is based on the determined position of the device and the registering of the volumetric medical imaging data with the further medical imaging data.

18. An apparatus according to claim 17, wherein the further medical imaging data comprises at least one of X-ray data, fluoroscopy data, digital angiography data, digital subtraction angiography data, CT data, cone-beam CT data, MRI data.

19. A navigation method for assisting navigation of a device through tissue, the method comprising:

receiving volumetric medical imaging data representative of an anatomical region, the anatomical region comprising a region of tissue to be traversed by a device;

processing the volumetric medical imaging data to identify different types of tissue in the region of tissue, wherein the different types of tissue comprise soft plaque and hard plaque;

determining a position of the device; and processing the volumetric medical imaging data to obtain a virtual endoscopic view of at least part of the region of tissue, the virtual endoscopic view comprising a virtual representation of the device in its determined position;

wherein the virtual endoscopic view is rendered such as to visually distinguish the identified different types of tissue, thereby assisting navigation of the device through the region of tissue.

20. An apparatus according to claim 1, wherein the different types of tissue in the region of tissue further comprises a vessel wall and an occlusion, wherein the virtual endoscopic view is rendered such as to visually distinguish the identified different types of tissue by rendering the occlusion as being semi-transparent and the vessel wall as opaque.

21. An apparatus according to claim 6, wherein the occlusion comprises the hard plaque.

* * * * *